United States Patent
DiMatteo et al.

(10) Patent No.: US 6,685,739 B2
(45) Date of Patent: Feb. 3, 2004

(54) IMPLANTABLE PROSTHETIC VALVE

(75) Inventors: Kristian DiMatteo, Watertown, MA (US); Peter Marshall, Newburyport, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/191,667

(22) Filed: Jul. 9, 2002

(65) Prior Publication Data

US 2002/0188348 A1 Dec. 12, 2002

Related U.S. Application Data

(62) Division of application No. 09/425,142, filed on Oct. 21, 1999, now Pat. No. 6,440,164.

(51) Int. Cl.$^7$ ............................... A61F 2/06; A61F 2/04
(52) U.S. Cl. ..................................... 623/1.24; 623/2.18
(58) Field of Search ............................... 623/1.24–1.26, 623/2.16, 2.17, 2.18; 604/9

(56) References Cited

U.S. PATENT DOCUMENTS

| | | |
|---|---|---|
| 15,192 A | 6/1856 | Peale |
| 4,759,759 A | 7/1988 | Walker et al. |
| 4,851,001 A | 7/1989 | Taheri |
| 5,123,919 A | 6/1992 | Sauter et al. |
| 5,358,518 A | 10/1994 | Camilli |
| 5,409,019 A * | 4/1995 | Wilk ........................... 128/898 |
| 5,413,599 A * | 5/1995 | Imachi et al. ............... 623/1.24 |
| 5,500,014 A | 3/1996 | Quijano et al. |
| 5,545,214 A | 8/1996 | Stevens |
| 5,759,830 A | 6/1998 | Vacanti et al. |
| 5,770,193 A | 6/1998 | Vacanti et al. |
| 5,770,417 A | 6/1998 | Vacanti et al. |
| 5,840,081 A | 11/1998 | Andersen et al. |
| 5,843,180 A | 12/1998 | Jaffe et al. |
| 5,851,232 A | 12/1998 | Lois |
| 5,855,597 A | 1/1999 | Jayaraman |
| 5,855,601 A | 1/1999 | Bessler et al. |
| 5,855,602 A | 1/1999 | Angell |
| 5,863,531 A | 1/1999 | Naughton et al. |
| 5,954,766 A | 9/1999 | Zadno-Azizi et al. |
| 5,957,949 A | 9/1999 | Leonhardt et al. |
| 6,015,431 A | 1/2000 | Thornton et al. |
| 6,027,525 A | 2/2000 | Suh et al. |
| 6,110,201 A | 8/2000 | Quijano et al. |
| 6,126,686 A | 10/2000 | Badylak et al. |
| 6,254,564 B1 | 7/2001 | Wilk et al. |
| 6,299,637 B1 * | 10/2001 | Shaolian et al. ........... 623/1.24 |
| 6,440,164 B1 * | 8/2002 | DiMatteo et al. ........... 623/1.24 |
| 6,458,153 B1 * | 10/2002 | Bailey et al. ............... 623/1.24 |
| 6,503,272 B2 * | 1/2003 | Duerig et al. ............... 623/1.24 |
| 6,530,952 B2 * | 3/2003 | Vesely ......................... 623/2.18 |

FOREIGN PATENT DOCUMENTS

| | | |
|---|---|---|
| EP | 0 520 126 A1 | 12/1992 |
| EP | 0 850 607 A1 | 7/1998 |
| FR | 2 788 217 | 7/2000 |
| WO | WO 94/04099 | 3/1994 |
| WO | WO 98/32400 | 7/1998 |

* cited by examiner

*Primary Examiner*—David H. Willse
*Assistant Examiner*—Suzette J. Jackson
(74) *Attorney, Agent, or Firm*—Hoffman & Baron, LLP

(57) ABSTRACT

A prosthetic valve for implantation within a fluid conducting lumen within a body includes an elongate generally cylindrical radially collapsible valve body scaffold defining a fluid passageway therethrough for retentive positioning within the lumen. A radially collapsible leaf valve member is supported by the scaffold includes a number of valve leafs deflectable between a closed position restricting fluid flow through the passageway and an open position permitting fluid flow through the passageway. The leaf valve member includes an interior leaf valve frame defining a valve leaf aperture which is sealed by a fluid impermeable non-thrombogenic lining to prevent fluid flow therethrough.

25 Claims, 7 Drawing Sheets

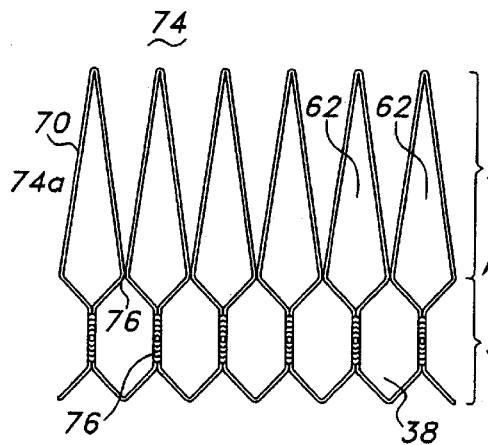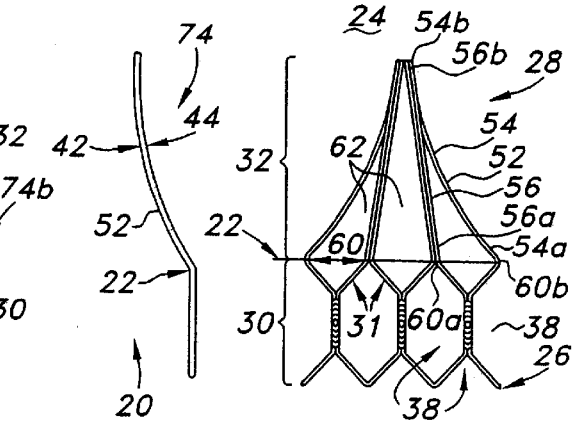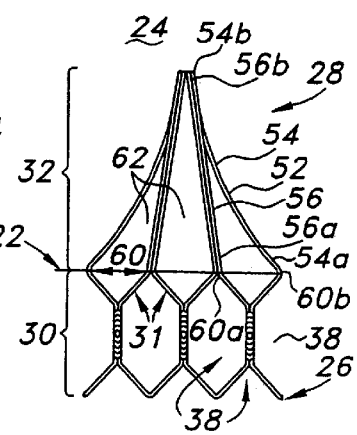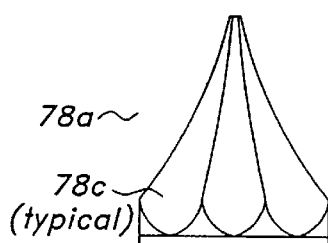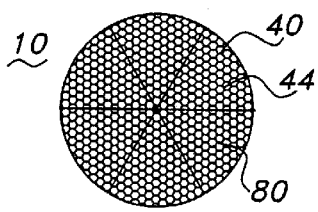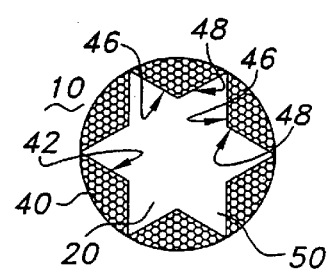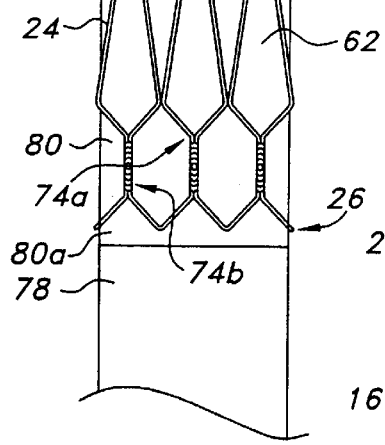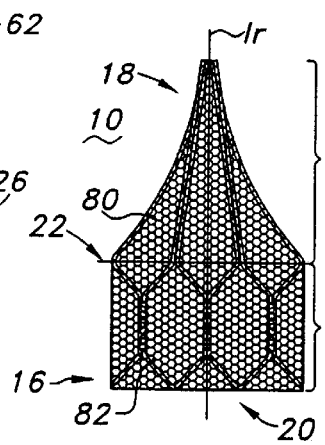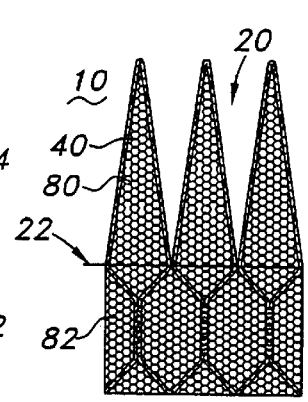

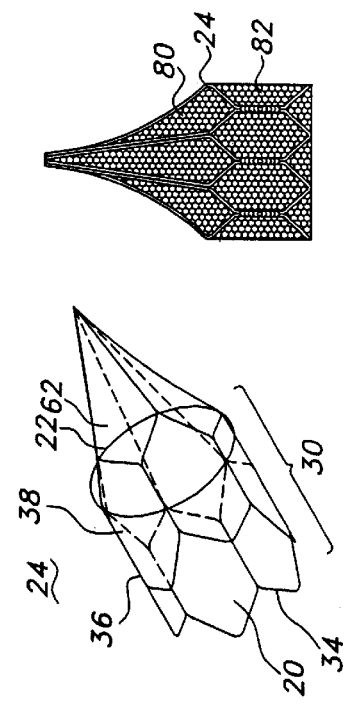
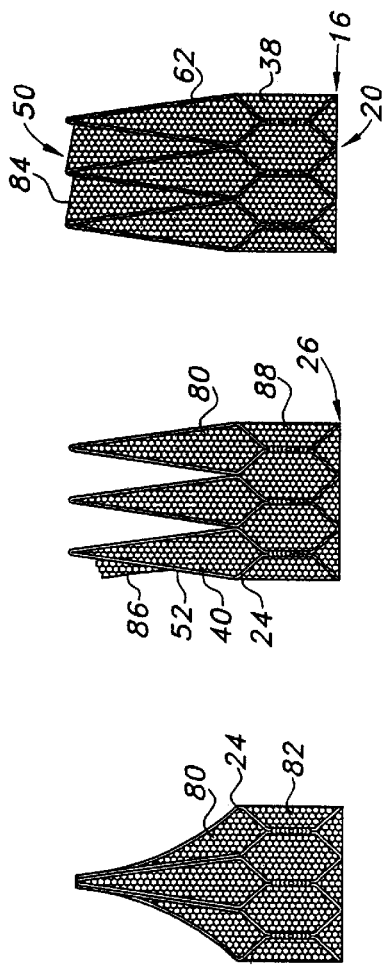
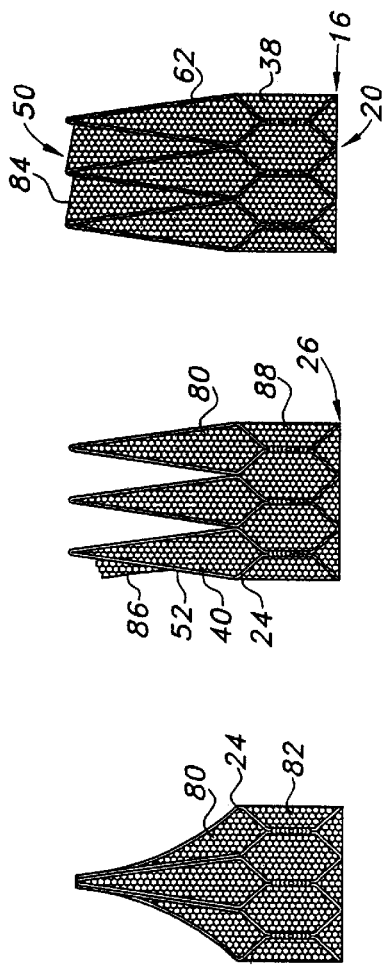
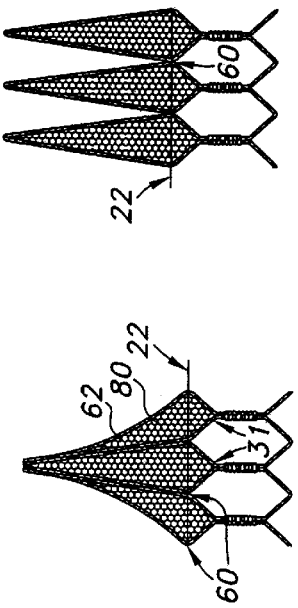
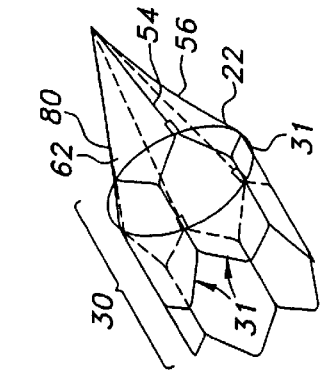
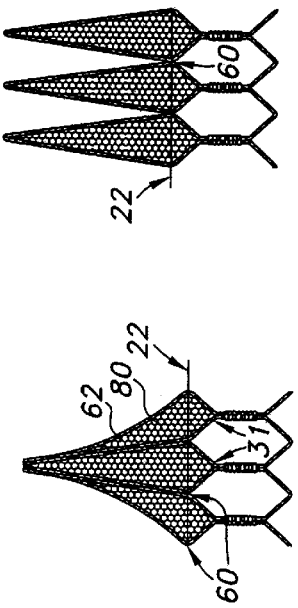
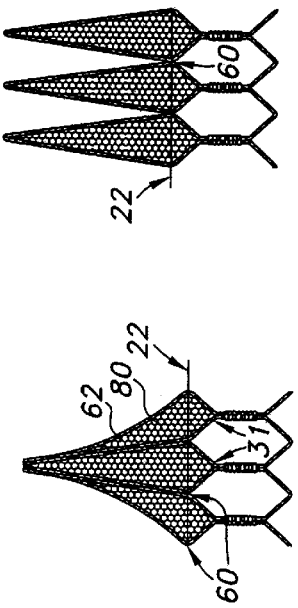

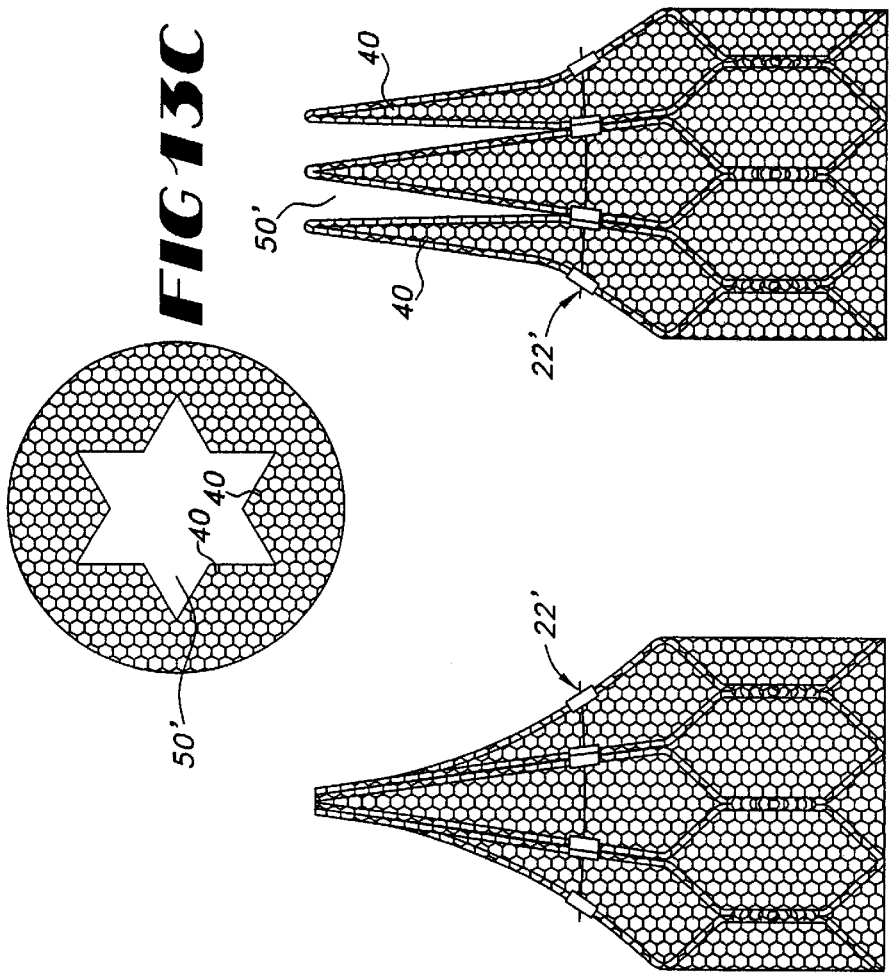

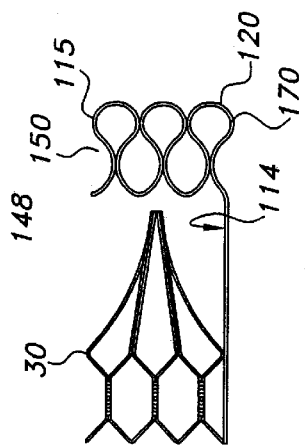
FIG 17
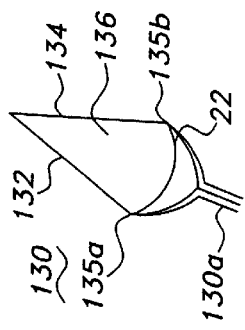
FIG 21
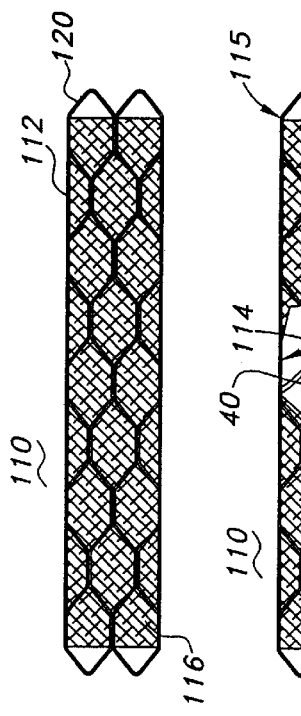
FIG 18
FIG 19
FIG 20

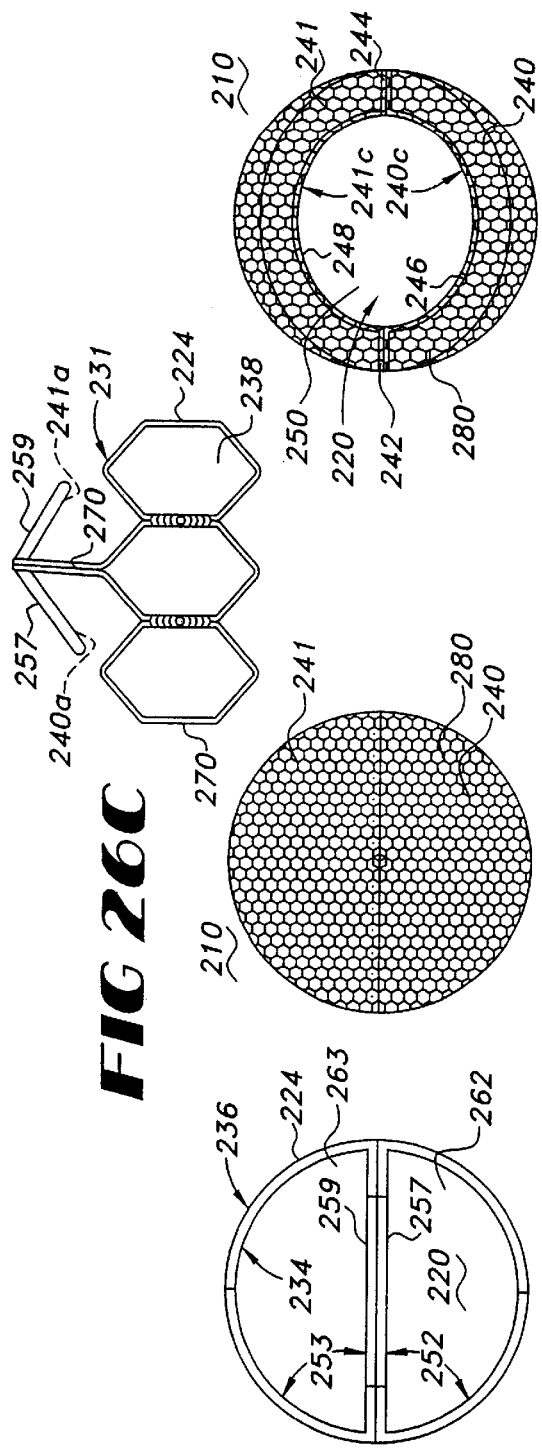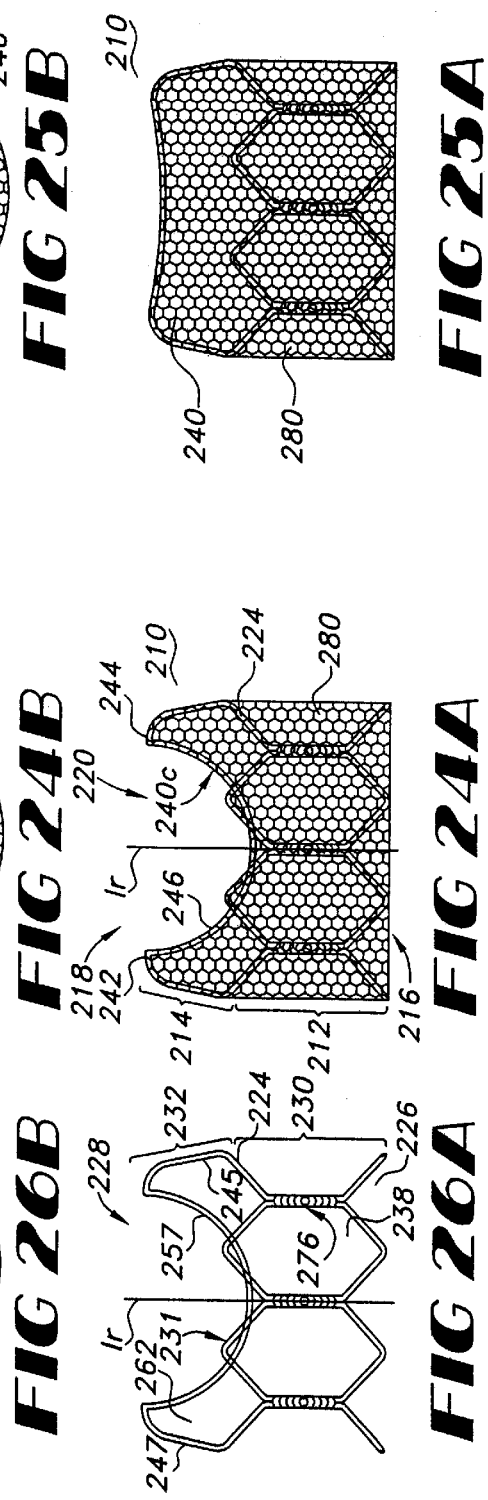

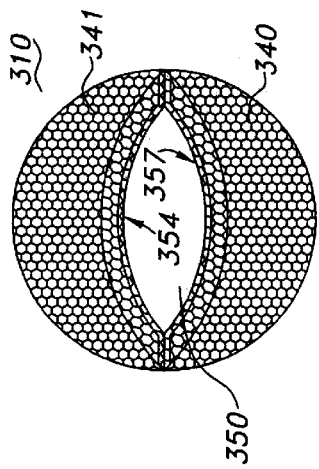
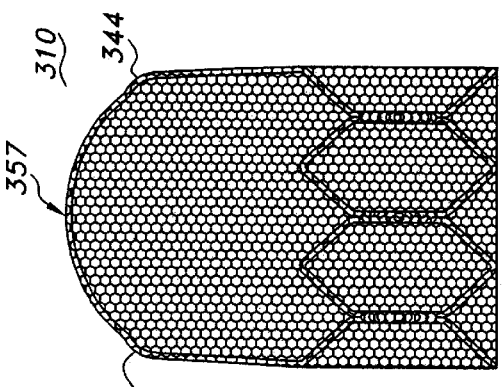
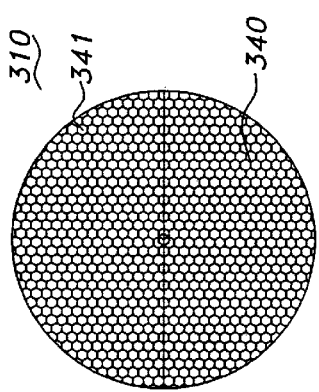
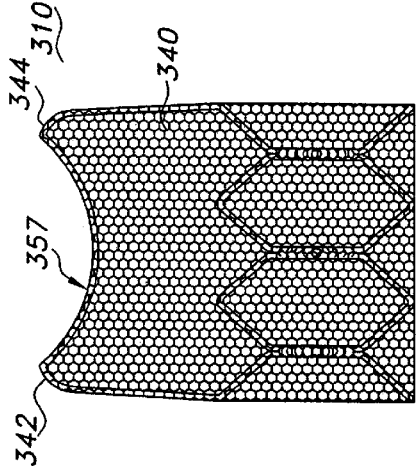
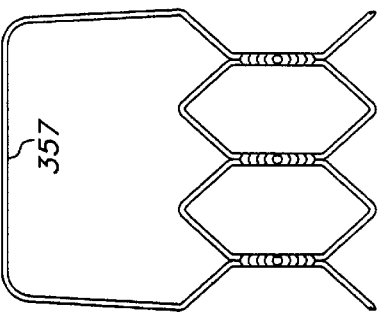
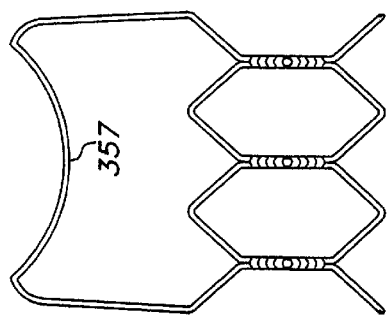

IMPLANTABLE PROSTHETIC VALVE

CROSS-REFERENCE TO RELATED APPLICATION

This application is a division of U.S. application Ser. No. 09/425,142, filed Oct. 21, 1999, now U.S. Pat. No. 6,440,164.

FIELD OF THE INVENTION

The present invention relates to the field of implantable prostheses. More specifically, the present invention relates to implantable prosthetic cardiac, aortic, and venous valves.

BACKGROUND OF THE INVENTION

In human pathology, the proper functioning of both cardiac and venous valves is of paramount importance. Disorders of cardiac valves cause significant morbidity and mortality. These disorders affect persons of all ages and can result from congenital or degenerative conditions, as well as from the sequelae of infections. Stenosis and insufficiency of the aortic or mitral valves have a greater incidence than stenosis and insufficiency of the tricuspid and pulmonary valves. Venous insufficiency is believed to contribute to various maladies, including edema, varicose veins, aching leg pain while standing, lipodermatosclerosis, and ulcerations. Venous insufficiency is essentially caused by venous hypertension and chronic venous stasis due to valvular incompetence both of an idiopathic nature and of a secondary nature following past illnesses of the venous systems.

A prosthetic cardiac or venous valve may regulate the direction of the pulsating blood flow so as to limit the occurrence of blood stasis in the region about the valve. By maintaining the direction of blood flow therethrough, a prosthetic cardia, aortic, or venous valve may alleviate the maladies resulting from valve disorders or venous insufficiency. A prosthetic valve should therefore permit blood flow in the proper predetermined direction to limit or prevent backflow of the blood in a reverse direction.

The art has seen several attempts for providing a prosthetic valve to alleviate the consequences of cardiac valve disorders and of venous insufficiency. These attempts generally fall into two categories, biologic valves and mechanical valves. Biologic valves are comprised of a stent supporting a number of circumferential leaflets made of a flexible material. If the material is biologic in nature, it may be either a xenograft, that is, harvested from a non-human cadaver, or an allograft, that is, harvested from a human cadaver. For example, it is known in the art to apply a pericardium biological tissue layer covering, for providing the valve leaflets, to a stent which provides structural annular integrity to the prosthesis. Non-biologic material such as polyurethane has also been used. The second category of prosthetic valves, mechanical valves, usually comprise a rigid annulus supporting up to three rigid leaflets. The annulus and leaflets are frequently formed in pyrolitic carbon, a particularly hard and wear resistant form of carbon. The annulus is captured within a sewing ring so that the valve may be attached to tissue at the location of the replaced valve. Unfortunately, surgically positioning these implants typically requires suturing or sewing the device into the blood vessel, increasing the risk of thrombosis due to the resulting suturing or anastomoses of the body vessel.

These attempts typically provide a valve structure having a relatively rigid tubular body structure which supports a flexible valve leaf structure. That is, any structural rigidity imparted to the tubular body structure is separated from the valve leaf structure. For example, U.S. Pat. No. 4,759,759 discloses a prosthetic valve having a solid stent member having a diametrically-opposed upstanding posts and a substantially cylindrical flexible cover. The two portions of the cover extending between the upstanding stent posts may be collapsed against each other in sealing registry over a fluid passageway defined by the stent. The stent, being a solid member, limits the radial collapsing thereof for endoscopic delivery within a body lumen. The cover, being unsupported by the stent within the fluid passageway of the valve, must itself provide sufficient strength and resiliency to optimally regulate fluid flow. Alternatively, U.S. Pat. No. 5,855,691 discloses a prosthetic valve having a radially expandable covered stent which defines an elongate fluid passageway therethrough. A flexible valve is disposed within the fluid passageway to regulate fluid flow therethrough. The valve is formed of a flexible and compressible material formed into a disc with at least three radial incisions to form deflectable leaflets. While the stent circumferentially supports the valve body, the leaflets are not supported by any other structure within the fluid passageway. There is therefore a need in the art for a unitary prosthetic valve construction which provides structural reinforcement to both the tubular body portion of the valve and to the valve leafs supported thereon.

SUMMARY OF THE INVENTION

The present invention is directed to providing a fully prosthetic valve having valve leafs formed from a covered valve leaf frame and which may be implanted using a minimally-invasive, endoscopic technique.

The present invention provides a prosthetic valve for implantation within a body lumen. The prosthetic valve of the present invention provides a device for regulating and maintaining the direction of a pulsating fluid flow through the body lumen. The valve includes a radially-collapsible scaffold portion and a radially-collapsible leaf valve portion. The scaffold portion includes a tubular open body scaffold defining a fluid passageway therethrough. The leaf valve portion is deflectable between a closed configuration in which fluid flow through the valve passageway is restricted and an open configuration in which fluid flow through the valve passageway is permitted.

Each of the valve leafs desirably includes a valve leaf frame having an open construction so as to facilitate radially-collapsing or -expanding the leaf valve portion of the valve. Each valve leaf frame defines a valve leaf aperture with the scaffold. The present invention seals each valve leaf aperture to prevent fluid flow therethrough. The material used to seal each valve leaf aperture is sufficiently thin and pliable so as to permit radially-collapsing the leaf valve portion for delivery by catheter to a location within a body lumen. A fluid-impermeable biocompatible non-thrombogenic valve leaf cover may be positioned on each valve leaf frame so as to seal the valve leaf aperture. The valve leaf cover may be formed from a surgically-useful textile such as Dacron, polyethlylene (PE), polyethylene terephthalate (PET), silk, Rayon, or the like. The valve leaf cover may also be formed of a surgically-useful polymeric material such as urethane, polytetrafluoroethylene (PTFE) or expanded polytetrafluoroethylene (ePTFE). The valve leaf cover may also coated with a cellular growth-inhibiting drug such as Heparin or Taxol or another such composition.

Similarly, each of the valve leaf apertures may be covered with cultured tissue cells derived from a either a donor or the host patient which are attached to the valve leaf frames. The cultured tissue cells may be initially positioned to extend either partially or fully into each valve leaf aperture. In order to provide additional support to the attached cultured tissue cells, a microfilter-type support mesh spanning the valve leaf aperture may also be provided. The present invention further contemplates that the supporting scaffold and valve leaf frames may be formed of either a bioabsorbable material or a non-bioabsorbable material. It is contemplated that the scaffold and valve leaf frames which are formed from a bioabsorbable material will eventually be displaced by the tissue cells as the tissue cells mature. Eventually the cells alone will provide the fully functioning valve. Alternatively, when the scaffold and valve leaf frames are formed from a non-bioabsorbable material, the cultured cells provide a means for reducing any undesirable biological response by the host.

The leaf valve member is normally spring biased towards the closed configuration. The present invention also contemplates biasing the leaf valve member towards the open configuration to simulate known anatomical mechanics of a valve in which the leaf valve portion would close upon experiencing sufficient back flow pressure from the direction downstream from the valve.

The leaf valve portion desirably includes a number of valve leafs which are deflected between the closed and open configurations when the fluid pressure differential thereacross exceeds a predetermined threshold. That is, the fluid pressure differential acts to open the valve when the fluid pressure upstream of the valve leaf portion is greater than the fluid pressure downstream of the valve leaf portion.

Each of the valve leafs is deflectably supported by the scaffold at a flexible hinge. The present invention contemplates that the open and closed configurations of the valve may be defined either downstream or upstream of the flexible hinges. It is desired that the scaffold portion of the valve will eventually provide fluid-tight engagement with the body lumen although it is contemplated that some leaking or fluid flow between the scaffold portion and the body lumen is still acceptable. Just as it is preferred, but not required, that the valve leafs prevent fluid flow in the closed configuration, it is recognized that substantial restriction of fluid flow past the scaffold-lumen interface may still provide a prosthetic valve exhibiting acceptable performance characteristics.

The present invention shows and describes both a bicuspid valve and a six-leaf valve, although designs employing a different number of valve leafs are clearly within the scope of the present invention. The bicuspid valve includes a pair of leaf frames which deflect about a hinge positioned downstream of the closable valve opening. The six-leaf variant includes valve leafs which deflect about hinges positioned upstream of the closable valve opening.

The abutting engagement between adjacent valve leafs, while desirably providing a fluid-tight seal, is contemplated to significantly restrict backflow past the valve leafs. The abutting engagement between adjacent valve leafs may therefore provide less than complete fluid integrity while still achieving the desired performance parameters.

The scaffold of the valve includes a first end defining a first opening, a second end defining a second opening, a substantially cylindrical interior face, a substantially cylindrical exterior face, and at least one radially-extending scaffold opening communicating between interior and exterior faces. The interior face generally defines the fluid passageway. The scaffold and leaf valve member are formed to be expandable from a first diameter permitting delivery through the body lumen to a second radially-expanded diameter for retentively engaging the body lumen at a desired location. The scaffold may be formed having a shape memory favoring radial self-expansion or may be formed so as to permit radial expansion by a delivery balloon which is deflated and withdrawn after scaffold expansion against the body lumen. The scaffold may further provide at least one radially outwardly projecting hook member for retentively engaging the fluid conduit when expanded thereagainst.

The present invention also contemplates forming both the scaffold and the valve leaf frames as a unitary support trellis. The unitary trellis may be formed by a single undulating wire bent to form both the radially expandable scaffold portion and the radially expandable valve leaf frames. While various configurations for the unitary support trellis of the present invention are contemplated, one preferred configuration bends a wire along a longitudinally extending and retracting undulating path so as to alternately define a collapsible and expandable leaf frame aperture and then a collapsible and expandable scaffold aperture. The wire may be laid along a flat surface so as to form a planar trellis preform. The trellis preform may then be wrapped about an elongate cylindrical mandrel. The valve leaf frames may be deflected about their respective hinges to establish a shape memory in either the open or closed configuration either prior to or after wrapping the trellis preform about the mandrel.

The trellis is desirably formed from a biocompatible metal or polymeric material. The trellis may additionally be formed from a shape-memory material to more reliably provide the required geometry to function effectively within the valve once radially expanded at a site within a lumen. The trellis may be formed from an alloy of nickel and titanium in specific proportions known in the art as nitinol. Alternatively, the trellis may be formed from a polymeric material which allows the trellis to be radially collapsed for delivery to a site in a lumen but then radially expands to return to an undeflected shape so as to function effectively within the valve.

The present invention also contemplates attaching an elongate generally cylindrical first biocompatible non-thrombogenic liner to the trellis. The first liner may be positioned on either the interior or exterior face of the scaffold. The first liner may also provide the sealing cover for the valve leaf frame apertures. The first liner may be trimmed to span between adjacent valve leafs in the open configuration so as to provide a larger surface area for the body fluid to act upon when urging the valve leafs between the open and closed configuration. The first liner may also be trimmed to provide at least one flap extending in the downstream direction beyond each valve leaf. Each flap may then be folded over the adjacent valve leaf frame and laminated through a valve leaf aperture to the liner.

Furthermore, an elongate generally cylindrical second biocompatible non-thrombogenic liner may be positioned on the scaffold opposite the first liner. The second liner may desirably extend only along a portion of the scaffold or fully along scaffold. The first and second liners may be joined so as to fully encase either just the scaffold or the entire trellis. It is contemplated that the first and second liners may be laminated together through one or more openings defined by the trellis. Additionally, the second liner may be formed by folding the first liner over the first end of the scaffold so as to extend at least partially along the opposite face of the scaffold as the first lining.

Each liner positioned on the trellis may inhibit thrombus formation and facilitate tissue ingrowth therethrough for assimilating the valve of the present invention into the body lumen. Towards this latter goal, one or both of the liners may be formed from a porous textile or polymeric material. It is further contemplated that either liner may be formed from an xenograft of cellular tissue from a donor such as bovine cardial tissue, or homograft of cellular tissue formed from the host patient.

It is also contemplated by the present invention that the prosthetic valve may also be attached to the interior surface of a second radially collapsible prosthetic fluid conduit. The second fluid conduit may be selected from many known stent and covered stent designs known in the art. The second fluid conduit further maintains the patency of the lumen to either side of the valve and may also include a biocompatible fluid impermeable non-thrombogenic lining on either or both of its own inner or outer surfaces. The materials used to form the second fluid conduit may also be selected to be either bioabsorbable or non-bioabsorbable as may be desired.

The present invention is also directed to methods of making the prosthetic valve of the present invention.

While the present invention has been described generally, the present invention will be more readily appreciated in a reading of the "Detailed Description of the Invention" with reference to the following drawings.

BRIEF DESCRIPTION OF THE DRAWINGS

FIG. 1 shows side elevational view of a prosthetic venous valve of the present invention in a closed, flow restricting configuration.

FIG. 2 shows a top elevational view of the prosthetic venous valve of FIG. 1 in the closed configuration.

FIG. 3 shows a side elevational view of the prosthetic venous valve of FIG. 1 in an open, flow conducting configuration.

FIG. 4 shows a top elevational view of the prosthetic venous valve of FIG. 1 in the open configuration.

FIG. 5 shows the unitary support trellis of the prosthetic venous valve of FIG. 1.

FIG. 6 shows a front elevational view of the unitary support trellis of the present invention in a flat trellis preform configuration.

FIG. 7 is a side elevational view of the unitary support scaffolding and valve leaflet frames upon being stressed to provide for a self-closing valve.

FIG. 8 depicts one step in a method of constructing the prosthetic valve of the present invention by wrapping the unitary support scaffolding and valve leaflet frames about a non-thrombogenic lining positioned about a mandrel.

FIG. 9 shows an isometric view of a unitary support trellis for a prosthetic valve of the present invention.

FIG. 10 shows a perspective view of a prosthetic valve of the present invention in an open configuration and in which the scaffold portion of the valve is substantially uncovered.

FIG. 11 shows a side elevational view of the prosthetic valve of FIG. 10.

FIG. 12 shows a side elevational view of the prosthetic valve of FIG. 10 in an open configuration.

FIGS. 13A–D depicts a further embodiment of the present invention in which adjacent leaf frames are joined at a location therealong to reduce the size of the valve flow opening.

FIG. 14 shows an embodiment a prosthetic valve of the present invention in which a unitary support trellis is positioned over a liner.

FIG. 15 shows an alternate embodiment of a prosthetic valve of FIG. 14 in which a second liner is positioned on the trellis to extend across the proximal end of the scaffold portion.

FIG. 16 is a side elevational view of an alternate embodiment of a prosthetic valve of the present invention in an open, flow-conducting configuration in which a non-thrombogenic webbing spans between each adjacent leaflet of the valve.

FIG. 17 shows an alternate embodiment of the present invention in which a secondary support scaffolding is formed to the downstream side of the valve leaflets.

FIG. 18 shows a still further embodiment of the present invention in which a number of deflectable valve leafs are attached within the fluid-conducting passageway to a radially-expandable prosthetic support structure.

FIG. 19 is a partial cut-away of the embodiment of FIG. 10 depicting the valve leaflets in a closed, flow-restricting configuration.

FIG. 20 is a partial cut-away of the embodiment of FIG. 11 depicting the valve leafs in an open, flow-conducting configuration.

FIG. 21 depicts an alternate embodiment of a covered valve leaf of the present invention to be attached to a radially expandable outer conduit.

FIGS. 24A–B are respective side and top elevational views of a prosthetic bicuspid valve of the present invention in the closed configuration.

FIGS. 25A–B are respective side and top elevational views of a prosthetic bicuspid valve of the present invention in the open configuration.

FIGS. 26A–B depict a unitary scaffold for the prosthetic bicuspid valve of FIG. 24 in the closed configuration.

FIG. 26C depicts the scaffold for the prosthetic bicuspid valve of FIG. 24 in the open configuration.

FIGS. 27A–B are respective side and top elevational views of another embodiment of the prosthetic bicuspid valve of FIG. 24, having a larger valve leaf and shallower valve cusp, in the closed configuration.

FIGS. 28A–B are respective side and top elevational views of the prosthetic bicuspid valve of FIG. 27A in the open configuration.

FIGS. 29A–B are side elevational views of the scaffold of the prosthetic bicuspid valve of FIG. 27A and FIG. 28A, respectively.

DETAILED DESCRIPTION OF THE INVENTION

Figures 22, 23:
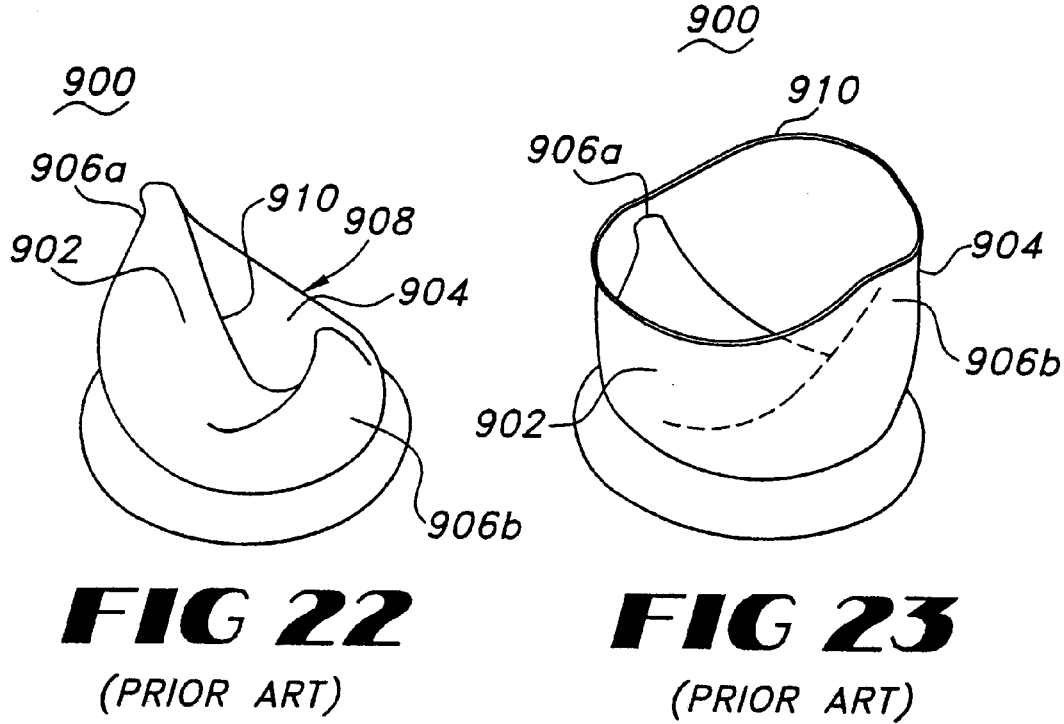
FIGS. 22 and 23 depict a prosthetic bicuspid valve of the prior art in the open and closed configurations, respectively.

The present invention relates generally to method and apparatus for providing a fluid flow check valve for a body lumen. A preferred embodiment of the present invention is particularly suitable for forming an endoluminal prosthetic valve for vascular applications. The prosthetic valve of the present invention regulates and maintains the direction of a pulsating fluid flow through a body lumen. The prosthetic valve of the present invention is configured to open and close in response to the fluid pressure differential across the valve. The valve includes a radially-collapsible scaffold portion and a radially-collapsible leaf valve portion which allows the valve to be delivered via catheter through the body lumen in which it will be emplaced. The scaffold portion includes a tubular open body scaffold defining a fluid passageway therethrough. The leaf valve portion is deflectable between a closed configuration in which fluid flow through the valve passageway is restricted and an open configuration in which fluid flow through the valve passageway is permitted.

The preferred embodiment of the prosthetic valve of the present invention is designed to be biased towards a closed, flow-restricting configuration. The valve opens when sufficient fluid pressure is applied to the leaflets from the upstream direction. Desirably the valve will open when the pressure differential across the leaflets reaches about 1–20 mm Hg. When the pressure differential is too low, the valve closes to prevent back flow. The valve desirably withstands up to about 100 mm Hg of back flow pressure. When the pressure differential from blood flowing the desired direction is removed, the valve returns to the closed configuration.

As will be described in further detail hereinbelow for the six-leaf variant of the present invention, the leaf valve portion is connected to the scaffold portion so that the valve leafs are deflectable about an annularly extending hinge line. The location of the hinge line along the length of the leaf valve portion influences the fluid pressure required to open and close the valve. In the closed configuration, the valve leaf portion substantially restricts fluid flow through the valve by providing a biocompatible impermeable non-thrombogenic covering extending from the hinge line in registry with the passageway.

Referring now to the drawings, FIGS. 1–5 depict a prosthetic valve 10 of the present invention. Valve 10 provides a radially-collapsible trellis 24 having an open construction. Trellis 24 includes an elongate tubular body scaffold 30 supporting a number of deflectable valve leaf frames 52 deflectable about a hinge line 22. Each valve leaf frame 52 defines a leaf frame aperture 62 which is sealed by a valve cover 80 positioned on trellis 24. The remainder of trellis 24 may also be covered with one or more liners 82 and 88, or may be left uncovered altogether. The covered leaf frames 52 form the deflectable valve leafs 40 which may be moved out of abutting engagement with each other so as to permit fluid flow through valve 10 in response to the fluid pressure upstream thereof.

Valve 10 is provided for implantation within the fluid passageway of a body lumen, such as for replacement of a cardial, arterial, or venous valve, to regulate the flow of a bodily fluid therethrough in a single direction. Valve 10 is constructed from biocompatible materials so as to minimize any adverse body reaction to the implantation of valve 10. Valve 10 includes an elongate tubular body portion 12 and a leaf valve portion 14. Valve 10 includes an upstream end 16, a downstream end 18, and an elongate fluid passageway 20 extending therebetween along a valve axis $l_v$. Leaf valve portion 14 is connected to body portion 12 to extend in overlying registry with passageway 20. Leaf valve portion 14 includes one or more valve leafs 40 which are deflectable with respect to body portion 12 about a hinge line 22 between a closed configuration, shown in FIGS. 1 and 2, restricting fluid flow through passageway 20, and an open configuration, shown in FIGS. 3 and 4, permitting fluid flow through passageway 20. As shown in FIGS. 13A–D, hinge line 22 may be alternatively formed along the length of valve portion 14 by joining adjacent valve leafs 40 at a midway location 22'. Locating hinge line 22 further downstream from body portion 12 increases the required higher fluid pressure differential to deflect the valve leafs to the open configuration.

Leaf valve portion 14 may provide any number of valve leafs 40. While six valve leafs are provided and discussed by reference to FIGS. 1–4, a bicuspid valve configuration is also contemplated and will be further discussed hereinbelow. Still referring to FIGS. 1–4, each of the valve leafs 40 are similarly-sized and -shaped and include opposed first and second major surfaces 42 and 44, respectively. Each first major surface 42 of a valve leaf 40 is oriented in facing opposition towards upstream end 16 of valve 10. Each of the valve leafs 40 provide a sawtooth perimetrical edge formed by a first and second leaf edge 46 and 48, respectively, which are positionable in abutting engagement with a leaf edge of an adjacent valve leaf 40 to define the closed configuration of valve 10. Similarly, as best shown in FIG. 4, the leaf edges 46 and 48 define a valve leaf opening 50 when in the open configuration. Valve leaf opening 50 is in fluid communication with passageway 20.

All of the valve leafs 40 are formed having a spring bias towards either the open or the closed configuration. When all of the valve leafs 40 are spring biased towards the closed configuration, the open configuration may be attained when the fluid pressure acting on the first major surfaces 42 of the valve leafs 40 overcomes both the fluid pressure acting on the second major surfaces 44 of the valve leafs 40 of valve 10 and any spring bias closing force imparted to the valve leafs 40 acting to close the valve leafs. Should the fluid pressure from the downstream end 28 of valve 10 become too great relative to the upstream fluid pressure, the valve leafs 40 will also be urged towards the closed configuration. Each valve leaf 40 desirably curves inward such that the second major surface 44 has a concave shape to better collect backflow and urge the valve leafs 40 towards the closed configuration. The prosthetic valve 10 of the present invention thereby provides a device for regulating and maintaining the direction of a pulsating fluid flow through the body lumen. While leaf valve portion 14 is normally spring biased towards the closed configuration, it is also contemplated, however, to bias leaf valve portion 14 towards the open configuration in order to simulate known anatomical mechanics of certain valves. Thus, when biased towards the open configuration, leaf valve portion 14 would close upon experiencing sufficient back flow pressure from the downstream end 28 of valve 10.

FIG. 5 shows the unitary support trellis 24 employed by valve 10. Trellis 24 may be formed from a material exhibiting shape memory characteristics or from a material which is readily expandable by a balloon catheter. Trellis 24 is generally an elongate tube being coaxial with valve axis $l_v$. Trellis 24 has opposed upstream and downstream ends 26 and 28. Upstream end 26 of trellis 24 is further defined by a radially collapsible body scaffold 30. Downstream end 28 of trellis 24 is further defined by a radially-collapsible leaf valve framework 32.

Trellis 24 may be formed from a wide variety of materials and in a wide variety of configurations. Radially-expandable endovascular stents known in the art provide useful basic designs for modification into a support trellis of the present invention and may be formed in a wide variety of configurations. One example of a stent useful in the present invention is a slotted tubular stent which is designed to radially expand either by balloon catheter or by forming the stent from a temperature-sensitive memory alloy which changes shape at a designated temperature or temperature range. Other stent types, such as tubular-shaped wire stents and self-expandable spring-biased stents are also contemplated. Trellis 24 may therefore be formed from a variety of materials including stainless steel, titanium, platinum, gold and other bio-compatible metals. Shape memory plastics, polymers, and thermoplastic materials which are inert in the body may also be employed to form trellis 24. Shaped memory alloys having superelastic properties generally made from specific ratios of nickel and titanium, commonly known as nitinol, are among the preferred trellis materials.

With additional reference to FIG. 9, scaffold 30 is a substantially cylindrical member having an interior face 34, an exterior face 36 and defines at least one radially-extending scaffold opening 38 communicating therebetween. Interior face 34 of scaffold 30 generally defines passageway 20. It is contemplated by the present invention that scaffold opening 38 need not be completely perimetrically bounded by scaffold 30. Scaffold 30 is formed to have a generally open configuration including a plurality of openings 38 communicating between interior face 34 and exterior face 36. These openings 38 provide for longitudinal flexibility of valve 10 as well as to permit valve 10 to be radially collapsed for delivery through, and radially expanded for deployment in, a body lumen such as a blood vessel. Furthermore, scaffold 30 preferably maintains a substantially coaxial alignment with the body lumen as leaf valve portion 14 deflects between the open and closed configurations so as to better seal passageway 20 when valve 10 is closed.

Leaf valve framework 32 includes a leaf frame 52 corresponding to each valve leaf 40 of leaf valve portion 14. Each leaf frame 52 includes a first and second elongate component legs 54 an 56, respectively. Each leaf frame 52 also has a length which is greater than the radius of the radially-expanded scaffold when implanted so as to minimize the risk of a valve leaf 40 over-deflecting about hinge line 22 towards upstream end 16 of valve 10. Each component leg 54 and 56 includes a proximal end 54a and 56a, and an opposed distal end 54b and 56b, respectively. Each leaf frame 52 is joined to scaffold 30 at a flexible hinge 60 defined by the junction of the proximal ends 54a and 56a of each leg component with scaffold 30. For each valve leaf 40, hinge 60 includes space-apart hinge components 60a, and 60b. Additionally, the distal ends 54b and 56b are contiguously formed. Each hinge component 60a, 60b may be respectively joined to the adjacent hinge component 60b, 60a of the adjacent leaf frame 52 in order to provide improved sealing of valve 10 in the closed configuration. The joining of the hinge components 60a and 60b of adjacent valve leafs 40 further defines annular hinge line 22.

Each leaf frame 52 defines a leaf frame aperture 62 with the distal extent 31 of scaffold 30. Leaf frame aperture 62 communicates between the first and second major surfaces 42 and 44 of valve leaf 40. The shape of leaf frame 52 is selected so as to assist and not inhibit the radial contraction of valve 10 for delivery via catheter through a body lumen. Additionally, leaf frame 52 is formed having a curve imparted thereto so as to provide a concave shape to second major surface 44 of leaf 40. Each leaf frame 52 is imparted with a shape memory so as to extend over passageway 20 in either the open or closed configuration.

Trellis 24 is preferably formed by a single wire 70 contoured to form both scaffold 30 and leaf valve frame 32. As shown in FIG. 6, wire 70 may trace a pattern on a flat surface so as to form a trellis preform 74. Wire 70 may be longitudinally extended and retracted in an undulating pattern such that a valve leaf frame aperture 62 is formed and then a scaffold opening 38 is formed, although other paths are possible. Each leaf frame aperture 62 and each scaffold opening 38 are perimetrically defined by a segment of wire 72 which allows trellis 24 to be radially-collapsible to allow delivery of valve 10 through a body lumen and then radially-expanded at a selected lumen site. Moreover, wire 70 may be welded, fused, crimped, sutured, or otherwise, joined together at strategic locations such as at a scaffold joint 76 defined between circumferentially-adjacent scaffold openings 38. Additionally, wire 70 may be joined at or about hinge joints 76 where adjacent hinge portions 60a and 60b of adjacent valve leaf frames abut.

Referring to FIGS. 7 and 8, trellis preform 74 is bent into the shape of trellis 24 by wrapping preform 74 about an elongate cylindrical mandrel 78 and joining trellis preform ends 74a and 74b together, and then deflecting the leaf frames 52 about hinge line 22 into overlying registry with passageway 20. Trellis 24 may be heat set in this configuration by a method as is typically known for the material which forms trellis 24.

The present invention seals each leaf frame aperture 62 to prevent fluid flow therethrough. The material used to seal each leaf frame aperture 62 is sufficiently thin and pliable so as to permit radially-collapsing the leaf valve portion for delivery by catheter to a location within a body lumen. Referring to FIGS. 10–12, a fluid-impermeable biocompatible non-thrombogenic valve leaf cover 80 may be positioned on trellis 24 so as to seal the leaf frame apertures 62. Preferably, valve leaf cover 80 seals the entire expanse of each leaf frame aperture 62 prior to implantation although it is recognized that the lumen wall will also assist in sealing leaf frame aperture 62 in the region about scaffold 30 adjacent hinge line 22. Therefore, valve leaf cover 80 should minimally seal leaf frame aperture 62 between component legs 54 and 56 and hinge line 22 so that as scaffold 30 becomes embedded in the lumen wall, valve 10 will fully seal at hinge line 22. Valve leaf cover 80 may be formed from a thin layer of, by way of illustration and not by limitation, PE, Pellethane, Urethane, bovine pericardial tissue, and the like. Alternatively, Valve leaf cover may be formed from a surgically-useful textile including, by way of illustration and not by limitation, Dacron, Polyethylene terephthalate (PET), Polyethlylene (PE), silk, Rayon, or the like. Valve leaf cover 80 may also be formed of a surgically-useful polymeric material including, by way of illustration and not by limitation, polytetrafluoroethylene (PTFE) or expanded polytetrafluoroethylene (ePTFE). Valve leaf cover 80 is desirably coated with a cellular growth-inhibiting drug such as Heparin or Taxol or the like.

Similarly, each valve leaf aperture 62 may be covered with cultured tissue cells derived from a either a donor or the host patient. The cultured tissue cells may be attached to each leaf frame 52 to the distal extent 31 of scaffold 30 so as to seal each valve leaf aperture 62. The cultured tissue cells may be initially positioned on a micro filter type mesh so as to extend either partially or fully into each valve leaf aperture 62. Scaffold 30 and leaf frames 52 may be formed of either a bioabsorbable material or a non-bioabsorbable material so that each will eventually be displaced by the tissue cells as the tissue cells mature. Eventually, then, the cells alone will provide the fully functioning valve. Alternatively, when scaffold 30 and leaf frames 52 are formed from a non-bioabsorbable material, the cultured cells provide a means for reducing any undesirable biological response by the host.

FIGS. 13A–D depict a still further embodiment of the present invention in which adjacent valve leaf frames 24 are joined at a location along the length thereof so as to provide a smaller opening 50' in the open configuration. Adjacent component legs 54 and 56 may be joined by welding or other techniques so as to form a hinge line 22' at a location downstream from the distal extent 31 of scaffold 30. As the size of opening 50' affects the required actuation pressure differential acting upon the valve leafs 40, it is contemplated that the precise location at which adjacent valve leaf frames 24 are joined may be selected in accordance with the fluid flow pressure parameters at the site within the body in which the valve of the present invention is emplaced.

Referring again to FIGS. 1–4 and with additional reference to FIGS. 14–16, an elongate generally cylindrical first biocompatible non-thrombogenic liner 82 is attached to trellis 24. First liner 82 may be positioned over either of interior face 34 or exterior face 36 of scaffold 30. First liner 82 may also be provided in addition to, or in place of, valve leaf cover 80 for sealing the leaf frame apertures 62. FIG. 15 depicts first liner 82 positioned on the interior 34 of scaffold 30. Furthermore, first liner 82 may be trimmed to conform closely to the valve leaf frames, as shown in FIG. 15. As shown by FIG. 16, first liner 82 may include a valve webbing 84 trimmed to span between the edges of adjacent valve leafs in the open configuration so as to provide a larger surface area for the body fluid to act upon when urging the valve leafs 40 between the open and closed configuration. First liner 82 may also be trimmed to provide at least one flap 86 extending in the downstream direction beyond each valve leaf 40. Each flap 86 may then be folded through the adjacent valve leaf aperture 62 and laminated to the first liner spanning the other major surface.

Similarly, an elongate generally cylindrical second biocompatible non-thrombogenic liner 88 may be positioned on scaffold 30 opposite first liner 82. Second liner 88 may extend only along a portion of scaffold 30, as shown in FIG. 15, or fully along trellis 24, as shown in FIG. 16. The first and second liners may be joined so as to fully encase either just scaffold 30 or all of trellis 24. Numerous techniques may be employed to laminate or bond first liner 82 to second liner 88 through the scaffold openings 38 and the leaf frame apertures 62 of trellis 34 including heat setting, adhesive welding, application of uniform force and other bonding techniques. Additionally, second liner 88 may be formed by folding an extended length of first liner 82 over upstream end 26 of scaffold 30 so as to extend at least partially along the opposite face of scaffold 30 as first liner 82.

Each of liners 82 and 88 may be capable of inhibiting thrombus formation. Additionally, liners 82 and 88 may either prevent or facilitate tissue ingrowth therethrough, as the particular application for the valve may dictate. For example, liner 88 may be formed from a porous material to facilitate tissue ingrowth therethrough while liner 80 is formed from a material or a treated material which inhibits tissue ingrowth. Liners 80 and 88 may be formed from a surgically-useful textile including, by way of illustration and not by limitation, Dacron, Polyethylene terephthalate (PET), Polyethlylene (PE), silk, Rayon, or the like. Valve leaf cover 80 may also be formed of a surgically-useful polymeric material including, by way of illustration and not by limitation, polytetrafluoroethylene (PTFE) or expanded polytetrafluoroethylene (ePTFE). It is further contemplated that either liner 82 and 88 may be formed from an xenograft of cellular tissue from a donor such as bovine cardial tissue, or homograft of cellular tissue formed from the host patient.

The polymeric liners 82 and 88 and valve cover 80 of the present invention may be formed by a variety of methods. For example, extrusion processes such as ram extrusion; polymeric casting techniques such as solvent casting and film casting; molding techniques such as blow molding, injection molding and rotational molding; and other thermoforming techniques useful with polymeric materials may be employed and chosen to best serve the type of material used and specific characteristics of the liner or cover desired.

While either or both of the polymeric liners 80 and 88 may be provided directly in tubular form, i.e as an extruded tube, either one or both can also be formed from extruded sheets of material which can be wrapped around all or a portion of the support scaffold to form a cover or liner. Combinations of sheets and tubes are also contemplated and may be applied to the support scaffold in a manner essentially as taught by U.S. patent application Ser. No. 09/035,501, which is herein incorporated by reference. For example, in one embodiment a sheet may be first formed and wrapped externally about the support scaffold and seamed along the longitudinal axis to form a cover. Such a sheet may be made with a high degree of uniaxial orientation. The relative axis of orientation of the stent may vary depending on the material used to form the liner or cover and the orientation and size of its pore structure. For example, in applicants' aforementioned copending U.S. application Ser. No. 08/721,834, the extruded material used to form the liner or cover may be formed from unsintered ePTFE sheets which have been expanded longitudinally and aligned generally longitudinally along the longitudinal stent axis, transverse to the longitudinal direction, or in an off-axis angle therebetween. In another example, a sheet or tube of ePTFE may be stretched and sintered several times to create a preformed ePTFE having expansion memory, such as shown in PCT Publication No. WO 96/00103 (U.S. application Ser. No. 0/95/07326), which is herein incorporated by reference. This publication is based on U.S. priority application Ser. No. 08/265,794, filed Jun. 27, 1994, which is also herein incorporated by reference. The preformed ePTFE allows for further expansion once the stent is implanted and radially deployed. Other embodiments of the present invention include the use of one or more tubes, providing a tube and a sheet formed into a tubular structure, or providing a plurality of sheets formed into a tubular structure on either surface of the stent.

Various bioeffecting agents may also be included in the liners by well known methods. For example, anti-infective agents and/or antithrombogenic agents may be coated on the liner or disposed within some of the pores of the polymeric cover or conformal layer prior to implantation. Additionally, such bioeffecting agents may also be employed on the stent or in the anchoring material used thereon. One example is shown in commonly assigned International Patent Application No. WO 95/29647, published on Nov. 9, 1995 and its U.S. priority Applications Ser. No. 235,300, filed Apr. 29, 1994, and Ser. No. 350,233, filed Dec. 1, 1994, which are incorporated herein by reference.

Referring again to FIG. 8, a method of forming a composite endoluminal device of the present invention includes the steps of providing an inner liner 82 on an elongate cylindrical mandrel 78. Trellis 24 is positioned over liner 82. Trellis 24 may be positioned over liner 82 such that an extent 80*a* of liner 82 may be folded over the upstream end 26 of trellis 24 and positioned over an extent of the exterior face of scaffold 30, as shown in FIG. 15. Extent 80*a* may be affixed to liner 82 through the scaffold openings 38 or affixed to scaffold 30 itself. Extend 80*a* may be positioned over the entire length of trellis 24, as shown in FIGS. 1 and 3. Alternatively, a second liner 88 may be positioned on trellis 24 opposite first liner 82.

Still referring to FIG. 8, mandrel 78 may be formed to include a shaped end 78*a* to serve as a die for shaping the closed configuration of the valve. Shaped end 78*a* includes a contoured impression 78*c* for each valve leaf 40. Each valve leaf 40 may be deflected against its contoured impression 78*c* to provide abutting engagement between the adjacent valve leafs. Trellis 24 may be shaped by shaped end 78a either prior to or after covering with liners 80 or 88. It may be desirable to impart the shape memory to trellis 24 prior attaching the liners. Additionally, while the leaf valve framework 32 is conformed to shaped end 78a, the valve leafs 40 may be joined in accordance with the embodiment of FIGS. 13A–D, either before or after attaching one or both of liners 80 and 88. It is further contemplated that each impression 78c may itself provide a contoured surface for imparting a curve to the deflected valve leafs 40.

The present invention further contemplates positioning trellis 24 about mandrel 78 without an underlying lining. Trellis 24 may then receive first lining over only the exterior face 36 of scaffold 30. Lining 80 may further be extended so as to cover the leaf frame apertures 62 of leaf valve frame 52, although it is contemplated using a different material to cover the leaf frame apertures 62. Lining 80 may also provide a valve webbing spanning between adjacent valve leafs 40.

It is additionally contemplated by the present invention to leave scaffold 30 substantially uncovered and to seal each leaf frame aperture 62 to the extent required to provide an acceptable degree of flow restriction in the closed configuration. While leaf frame apertures 62 are desirably fully sealed prior to implantation, it is contemplated that only that portion of leaf frame aperture 62 which extends in registry with fluid passageway 20 be sealed by one or more liners 80. The embedding of scaffold 30 into the body lumen would thereby provide valve 10 with an acceptable degree of fluid-integrity about the lumen wall. In such an embodiment, valve leaf cover 80 may be applied to trellis 24 to fully seal leaf frame aperture 62. The preferred method includes attaching a cover to both frame component legs 54 and 56 and to the segment of distal scaffold extent 31 between the corresponding hinges.

Liners 82 and 88 may be formed of a polymeric material which may be fused by various techniques such as heat sealing, solvent bonding, adhesive bonding, or use of coatings. It is also contemplated that liners 80 and 88 may be formed of a textile material, or that each could include a homograft or xenograft tissue retained by the intermediate member to seal the openings in same. The formation, application, and orientation of liners 80 and 88 may be accomplished by the techniques described in commonly-assigned and copending U.S. patent application Ser. No. 09/035,501, entitled "Conformal Laminate Stent Device", which is incorporated by reference herein.

FIG. 17 shows an alternate embodiment of a trellis 148 for valve 110 in which trellis 30 of valve 10 is mechanically joined to a second radially collapsible scaffold 150. It is also contemplated that trellis 30 of valve 10 may be continuously formed by the same wire 170 which forms second scaffold 150. The present invention contemplates that elongate portions 170a of wire 170 may be employed between sections of scaffolds to allow the prosthetic valve 10 to be emplaced within tortuously-extending sections of body lumen.

FIGS. 18–21 depict yet another embodiment of the present invention in which the valve leafs of an implantable prosthetic valve 110 are attached to the interior lumenal surface 114 of a second radially collapsible tubular fluid conduit 112. Second conduit 112 may be selected from many known stent and covered stent designs known in the art. Second conduit 112 further maintains the patency of the body lumen to either side of valve 10 and may also include a biocompatible fluid impermeable non-thrombogenic lining 116 on either or both of its own interior or exterior lumenal surfaces, 114 and 115, respectively. The materials used to form the second tubular fluid conduit may also be selected to be either bioabsorbable or non-bioabsorbable as previously described for liners 80 and 88.

Second conduit 112 includes a radially collapsible skeleton 120 which may be formed from a shape memory alloy, an elastic metal, or a polymer. Second conduit 112 may also be formed of a bioabsorbable material. Outer surface 115 of second conduit 112 need not be covered as skeleton 120 will eventually embed into the lumen wall, but a lining 116 may be preferable so as to limit flow-around until that time.

As shown in FIG. 19, a non-absorbable tether line 125 may have ends 125a and 125b affixed between second conduit 112 and each valve leaf 40 to prevent the leafs from inverting towards the upstream end 126 of secondary conduit should the back flow pressure become sufficient to over-deflect the leafs past hinge line 22. Tether line 125 is desirably affixed at ends 125a and 125 to non-bioabsorbable components of valve 110.

With additional reference to FIG. 21, it is also contemplated by the present invention to mechanically attach a number of covered leaf frames 130 to the interior lumenal surface 114 of second conduit 112. Covered leaf frames 130 are similar in construction to valve leafs 40 of valve 10. Each covered leaf frame 130 includes a first and second elongate component leg 132 and 134 welded or otherwise affixed to skeleton 120 at a hinge portion 135 comprising hinges 135a and 135b where the component legs attach. Covered leaf frame 130 defines a leaf frame aperture 136 with skeleton 120 between the associated hinges 135a and 135b. A leaf cover 140 is desirably affixed over each leaf frame aperture 136 by spanning from each component leg 132 and 134 to skeleton 120 between the hinges 135a and 135b so as to provide a fluid integrity to the valve in the closed configuration. Alternatively, the covered leaf frames could be attached to surface 114 along a leaf frame stem 130a.

Referring now to FIGS. 22 and 23, a prosthetic bicuspid valve 900 of the prior art is depicted. Valve 900 is typical of a bubble valve design which provides first and second valve leafs, 902 and 904. Valve 900 is formed having a solid interior stent frame which provides a pair of opposed raised posts which form raised hubs 906a and 906b. The interior stent is covered with a generally cylindrical cover 908 which itself is formed of a flexible material. Valve flaps 902 and 904 are formed by the portion of cover 908 extending unsupported beyond the interior stent structure. Valve flaps 902 and 904 must therefore rely on the resiliency and shape memory of the material of the cover 908 for any bias towards the open or closed configurations. As shown in FIG. 23, cover 908 terminates at a flap edge 910 which, in the open configuration, defines a substantially circular opening through valve 900. In the closed configuration, shown in FIG. 22, flap edge 910 extends along a substantially catenary path between raised hubs 906a and 906b to seal valve 900.

FIGS. 24A–26 depict a prosthetic bicuspid valve 210 of the present invention. With like numbers indicating like components to other embodiments of the present invention, bicuspid valve 210 is a bubble valve including a support trellis 224 and a fluid impermeable non-thrombogenic lining 280. Valve 210 is contemplated as a replacement aortic valve. Valve 210 is constructed from biocompatible materials so as to minimize any adverse body reaction to its implantation.

Valve 210 includes an elongate tubular body portion 212 and a leaf valve portion 214. Valve 210 includes an upstream end 216, a downstream end 218, and an elongate fluid passageway 220 extending therebetween along a valve axis $l_v$. Leaf valve portion 214 extends in overlying registry with passageway 220 and includes first and second valve leafs 240 and 241 which are deflectable between a closed configuration, shown in FIGS. 24A and 24B, restricting fluid flow through passageway 220, and an open configuration, shown in FIGS. 25A and 25B, permitting fluid flow through passageway 220. Valve 210 also includes a pair of diametrically-opposed valve hinge hubs 242 and 244 about which valve leafs 240 and 241 deflect between the open and closed configurations. Hinge hubs 242 and 244 are located downstream of valve leafs 240 and 241 when valve 210 is in the closed configuration.

Valve leafs 240 and 241 are similarly-sized and -shaped and include opposed first and second major surfaces 240a, 241a and 240b, 241b, respectively. Each first major surface 240a, 241a of a valve leaf 240 is oriented in facing opposition towards upstream end 216 of valve 210. Valve leafs 240 and 241 further include an arcuate leaf edge 240c and 241c, respectively, which are positionable in abutting engagement along a substantially catenary curve between hinge hubs 242 and 244 to define the closed configuration of valve 210. Similarly, as best shown in FIG. 4, the leaf edges 240c and 241c define an eye-shaped valve leaf opening 250 when in the open configuration. Valve leaf opening 250 is in fluid communication with passageway 220. Whereas the valve leafs of the sawtooth valves of the present invention desirably had a longitudinal length greater than the radius of the implanted scaffold, valve leafs of the biscupid valves of the present invention may be formed having a longitudinal length dimension 1 which is smaller than the radius of the implanted scaffold portion.

Valve leafs 240 and 241 are desirably formed having a spring bias about hinge hubs 242 and 244 towards the closed configuration. The open configuration may be attained when the fluid pressure acting on the first major surfaces 240a and 241a of the valve leafs 240 and 241 overcomes both the fluid pressure acting on the second major surfaces 240b and 241b of the valve leafs 240 of valve 210 and the spring bias imparted to the valve leafs 240 acting to close the valve leafs. Similarly, when the fluid pressure from the downstream end 218 of valve 210 become too great relative to the upstream fluid pressure, the valve leafs 240 will be urged towards the closed configuration to thwart fluid flow through the valve back towards the upstream end 228.

FIGS. 26A–C show the support trellis 224 employed by valve 210. Trellis 224 may be formed from a material exhibiting shape memory characteristics or from a material which is readily expandable by a balloon catheter. Trellis 224 is generally an elongate tube being coaxial with valve axis $l_v$. Trellis 224 has opposed upstream and downstream ends 226 and 228. Upstream end 226 of trellis 224 is further defined by a radially collapsible body scaffold 230. Downstream end 228 of trellis 224 is further defined by a radially-collapsible leaf valve framework 232.

Trellis 224 may be formed from a wide variety of materials and in a variety of configurations. Radially-expandable endovascular stents known in the art provide useful basic designs for modification into a support trellis of the present invention and may be formed in a wide variety of configurations. One example of a stent useful in the present invention is a slotted tubular stent which is designed to radially expand either by balloon catheter or by forming the stent from a temperature-sensitive memory alloy which changes shape at a designated temperature or temperature range. Other stent types, such as tubular-shaped wire stents and self-expandable spring-biased stents are also contemplated.

Trellis 224 may therefore be formed from a variety of materials including stainless steel, titanium, platinum, gold and other bio-compatible metals. Shape memory plastics and thermoplastic materials which are inert in the body may also be employed to form trellis 224. Shaped memory alloys having superelastic properties generally made from specific ratios of nickel and titanium, commonly known as nitinol, are among the preferred trellis materials.

Scaffold 230 is a substantially cylindrical member having an interior face 234, an exterior face 236 and defines at least one radially-extending scaffold opening 238 communicating therebetween. Interior face 234 of scaffold 230 generally defines passageway 220. It is contemplated by the present invention that scaffold opening 238 need not be perimetrically bounded by scaffold 230. Scaffold 230 is formed to have a generally open configuration including a plurality of openings 238 communicating between interior face 234 and exterior face 236. These openings 238 provide for longitudinal flexibility of valve 210 as well as to permit valve 210 to be radially collapsed for delivery through, and radially expanded for deployment in, a body lumen such as a blood vessel. Furthermore, scaffold 230 preferably maintains a substantially coaxial alignment with the body lumen as leaf valve portion 214 deflects between the open and closed configurations so as to better seal passageway 220 when valve 210 is closed.

Leaf valve framework 232 includes leaf frames 252 and 253 corresponding to valve leafs 240 and 241. Leaf frames 252 and 253 define leaf frame apertures 262 and 263 with the distal extent 231 of scaffold 230. Leaf frame apertures 262 and 263 communicate between first and second major surfaces 240a and 240b of valve leaf 240, and first and second major surfaces 241a and 241b of valve leaf 241, respectively. Leaf frames 252 and 253 may be radially contracted towards valve axis $l_v$ for delivery via catheter through a body lumen. Leaf frames 252 and 253 are imparted with a shape memory so as to extend over passageway 220 once implanted in a body lumen.

Leaf valve framework 232 further includes diametrically opposed hinge posts 245 and 247 extending from distal end 231 of scaffold 230 towards hinge hubs 242 and 244, respectively. Hinge hubs 242 and 244 extend transversely to valve axis $l_v$. Arcuate frame portions 257 and 259 of valve leafs 240 and 241 extend between hinge hubs 242 and 244 along a substantially catenary path. As shown in FIGS. 25B and 26C, arcuate frame portions 257 and 259 deflect about hinge hubs 242 and 244 and swings towards and away from each other as valve leafs 240 and 241 are urged between the closed and open configurations.

Each leaf frame aperture 262 and each scaffold opening 238 are perimetrically defined by a segment of wire 270 which allows trellis 224 to be radially-collapsible so as to allow delivery of valve 210 through a body lumen and then radially-expanded at a selected lumen site. Moreover, wire 270 may be welded, fused, crimped, sutured, or otherwise, joined together at strategic locations, such as at a scaffold joint 276 defined between circumferentially-adjacent scaffold openings 238.

Trellis 224 is preferably formed by a single wire 270 contoured to form both scaffold 230 and leaf valve frame 232. Wire 270 may be longitudinally extended and retracted in an undulating pattern such that one half of scaffold 230 is formed and a then a portion or all of valve leaf frame 232 prior to completing scaffold 230, although other paths are possible. Alternatively still, trellis 224 may be formed in constituent components which are then joined. Other methods for forming trellis 224 as a unitary member will thus be apparent to those skilled in the art.

Liner 280 may be formed in accordance with the description for liner 80 hereinabove. Liner 280 may be applied to trellis 224 at either interior face 234, exterior face 236, or at both faces. Liner 280 may further be affixed only to trellis 224 or may include portions which are adhered to itself through the scaffold openings 238 and/or the leaf frame apertures 262 and 263. It is contemplated that one of inner liner 280*a* and outer liner 280*b* may be forced though trellis 224 to be affixed to the other or both may be joined together within the scaffold openings 238 or the leaf frame apertures 262, 263.

The present invention further contemplates that the liner 280 forming the major surfaces of valve leafs 240 and 241 are urgable into a concave shape so as to better collect backflow and urge the valve leafs towards the open or closed configuration. The major surfaces of valve leafs 240 and 241 have complex shapes which are a function of the longitudinal spacing of catenary frame portion from distal end 231 of scaffold 230. Furthermore, the material forming the major surfaces need not taughtly-extend across the leaf frame openings of valve leafs 240 and 241. The present invention contemplates providing sufficient excess material spanning leaf frame apertures 262 and 263 such that overwhelming fluid pressure acting on one major surface of a valve leaf forces the covering through the valve leaf opening. When excess material is applied across valve leaf apertures 262 and 263, then the first major surfaces of each valve leaf 240 and 241 may assume a concave shape so as to favor the opening the valve leafs and the second major surfaces may assume a concave shape so as to favor closing the valve leafs.

FIGS. 27A–29B depict an alternate embodiment of a bicuspid valve of the present invention. Valve 310 is similar in most respects to valve 210 described hereinabove but includes valve leafs 340 and 341 defined by leaf frame edges 357 and 359 having larger radius of curvature between hinge hubs 342 and 344 than is shown in FIGS. 2–5. The larger radius of curvature along leaf frame edges 357 and 359 results in larger major surfaces for the opposed valve leafs 340 and 341 and defines a smaller opening 350 in the open configuration, as shown in FIG. 28B. It is contemplated that leaf frame edges 357 and 359 are deflectable to a position coextensive with hinge hubs 342 and 344, as shown in FIG. 29B, or to a position downstream of hinge hubs 342 and 344, as shown in FIG. 28B. It is also contemplated that the major surfaces 340*a* and 341*a* may come into contact when valve leafs 340 and 341 are in the closed configuration.

While the present invention has been shown and described in detail above, it will be clear to the person skilled in the art that changes and modifications may be made without departing from the spirit and scope of the invention. That which is set forth in the foregoing description and accompanying drawings is offered by way of illustration only and not as a limitation. The actual scope of the invention is intended to be defined by the following claims.

What is claimed is:

1. A method of forming a prosthetic valve for implantation within a body lumen, comprising providing a radially collapsible trellis having a tubular body scaffold portion defining an elongate fluid passageway for fluid flow therethrough and a valve leaflet frame portion having a number of valve leaf frames each defining a valve leaf frame aperture with the scaffold portion wherein said valve leaf frames are deflectable with respect to said scaffold portion so as to extend in overlying registry with the passageway between a first position and a second position, and sealing each said valve leaf aperture with a biocompatible non-thrombogenic fluid impermeable material such that when the leaflet portion is in said first position, fluid flow through said passageway is substantially restricted.

2. The method of forming a prosthetic valve of claim 1, further comprising the steps of biasing each of said valve leaf frames towards the first position.

3. The method of forming a prosthetic valve of claim 1, further comprising the step of biasing said valve leaflet portion towards the second position whereby fluid flow through said passageway is permitted.

4. The method of forming a prosthetic valve of claim 1, further comprising the step of coating the material sealing each said valve leaf frame aperture with a growth inhibiting drug.

5. The method of forming a prosthetic valve of claim 1, further comprising the steps of providing an elongate mandrel having a cylindrical outer surface;

positioning a first biocompatible non-thrombogenic fluid impermeable liner over the outer surface of the mandrel;

positioning said trellis over said first liner; and affixing said first liner to said trellis.

6. The method of forming a prosthetic valve of claim 1, further comprising the step of forming a radially collapsible trellis having a shape memory.

7. The method of forming a prosthetic valve of claim 6, wherein the step of forming a radially collapsible trellis further includes laying a wire in an undulating manner in the shape of a preform of the trellis.

8. The method of forming a prosthetic valve of claim 7, wherein the laying step further comprises the steps of alternately forming an aperture defined by a valve leaflet frame and said body scaffold and forming an opening defined by said scaffold portion.

9. The method of forming a prosthetic valve of claim 1, further comprising the step of deflecting each said leaflet frame portion with respect to the body scaffold portion component to impart a shape memory to the preform in one of said first and second positions.

10. The method of forming a prosthetic valve of claim 9, further comprising the step of imparting a curve to the leaflet frame.

11. The method of forming a prosthetic valve of claim 9, wherein the imparting step further comprises the step of heat setting a shape memory alloy at a temperature above its austenitic start temperature in a desired shape.

12. The method of forming a prosthetic valve of claim 5, further comprising the step of positioning a second biocompatible fluid impermeable non-thrombogenic liner over the scaffold.

13. The method of forming a prosthetic valve of claim 12, further comprising the step of positioning said second fluid impermeable liner opposite said first liner.

14. The method of forming a prosthetic valve of claim 12, further comprising the step of positioning said second fluid impermeable liner to be substantially longitudinally coextensive with said first liner along said scaffold portion.

15. The method of forming of prosthetic valve of claim 14, wherein said step of positioning said second fluid impermeable liner opposite said first liner and substantially coextensive with said first liner along said scaffold portion further comprises positioning said second liner over said valve frame portion.

16. The method of forming a prosthetic valve of claim 1, further comprising the step of providing anchoring means to the prosthesis for engaging a lumen wall upon emplacement at a selected site of a body lumen.

17. The method of forming a prosthetic valve of claim 1, further comprising the step of providing an elongate mandrel having a cylindrical outer surface;

positioning said trellis over the outer surface of said mandrel; and positioning a first biocompatible non-thrombogenic fluid impermeable liner over the outer surface of said trellis.

18. The method of forming a prosthetic valve of claim 1, further comprising the step of incorporating cultured tissue cells into said valve frame aperture.

19. The method of forming a prosthetic valve of claim 18, further comprising the step of covering each said valve leaf frame with cultured tissues.

20. The method of forming a prosthetic valve of claim 18, further comprising the step of forming each said valve leaf frame from a bioabsorbable material to be displaced by said cultured tissue cells upon said cells maturing within the body lumen.

21. The method of forming a prosthetic valve of claim 18, further comprising the step of forming said trellis from a bioabsorbable material.

22. The method of forming a prosthetic valve of claim 18, further comprising the step of forming said trellis from a metallic material.

23. The method of forming a prosthetic valve of claim 22, further comprising the step of forming said trellis from a shape memory material selected from the group consisting of an alloy of nickel and tin and a polymeric material.

24. The prosthetic valve of claim 1, further including a second radially collapsible open tubular scaffold having a cylindrical inner surface and an opposing cylindrical outer surface, said inner surface defining an elongate fluid conduit being substantially coaxially-aligned with said passageway of said valve, said second scaffold affixed to said body scaffold and extending at least one of said upstream and downstream direction from said valve.

25. The prosthetic valve of claim 1, wherein said second scaffold further includes a biocompatible fluid impermeable non-thrombogenic lining on at least one of said inner surface and said outer surface.

* * * * *